United States Patent
Masuda et al.

(10) Patent No.: US 12,062,171 B2
(45) Date of Patent: Aug. 13, 2024

(54) ULTRASONIC DIAGNOSTIC DEVICE AND STORAGE MEDIUM

(71) Applicant: CANON MEDICAL SYSTEMS CORPORATION, Otawara (JP)

(72) Inventors: Takashi Masuda, Utsunomiya (JP); Tomio Nabatame, Otawara (JP); Takeshi Sugio, Otawara (JP); Asuka Ozawa, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 63 days.

(21) Appl. No.: 17/447,010

(22) Filed: Sep. 7, 2021

(65) Prior Publication Data

US 2022/0076419 A1 Mar. 10, 2022

(30) Foreign Application Priority Data

Sep. 8, 2020 (JP) .................. 2020-150258

(51) Int. Cl.
*G06T 7/30* (2017.01)
*A61B 8/00* (2006.01)
(Continued)

(52) U.S. Cl.
CPC .......... *G06T 7/0014* (2013.01); *A61B 8/4444* (2013.01); *G06T 7/30* (2017.01);
(Continued)

(58) Field of Classification Search
CPC .............. G06T 7/0014; G06T 7/30; G06T 2207/10132; G06T 2207/30004;
(Continued)

(56) References Cited

U.S. PATENT DOCUMENTS 7,965,907 B2 * 6/2011 Takekoshi .............. G16H 30/20
358/404
2004/0146190 A1 * 7/2004 Kasai ..................... H04L 67/61
382/128
(Continued)

FOREIGN PATENT DOCUMENTS

JP 3842730 B2 11/2006
JP 2010-253031 A 11/2010
(Continued)

OTHER PUBLICATIONS

Japanese Office Action issued Mar. 12, 2024 in Japanese Patent Application No. 2020-150258, 4 pages.

*Primary Examiner* — Alexei Bykhovski
(74) *Attorney, Agent, or Firm* — Oblon, McClelland, Maier & Neustadt, L.L.P.

(57) ABSTRACT

An ultrasonic diagnostic device of an embodiment includes processing circuitry. The processing circuitry acquires an ultrasonic image of a subject, executes processing for each step for each of one or more examination procedures registered in advance and including one or more steps including processing of acquiring the ultrasonic image, in which set images are associated and registered, and determines a recommended step recommended to be executed subsequent to a current step or instead of the current step on the basis of a degree of consistency between a set image registered for each step and an ultrasonic image acquired in the current step that is being executed, and executes the recommended step subsequent to the current step or instead of the current step when the recommended step has been determined during execution of the current step.

6 Claims, 8 Drawing Sheets

(51) Int. Cl.
*G06T 7/00* (2017.01)
*G16H 30/40* (2018.01)

(52) U.S. Cl.
CPC ............... *G06T 2207/10132* (2013.01); *G06T 2207/30004* (2013.01); *G16H 30/40* (2018.01)

(58) Field of Classification Search
CPC ... G06T 7/0012; A61B 8/4444; A61B 8/4405; A61B 8/4254; A61B 8/4263; A61B 8/54; A61B 8/4245; G16H 30/40; G16H 40/20
See application file for complete search history.

(56) References Cited

U.S. PATENT DOCUMENTS

| | | | | |
|---|---|---|---|---|
| 2006/0173713 | A1* | 8/2006 | Petro | G16H 10/60 |
| | | | | 705/2 |
| 2012/0157843 | A1* | 6/2012 | Lavin | G01S 7/52098 |
| | | | | 600/443 |
| 2017/0256082 | A1* | 9/2017 | Nabatame | G06T 11/60 |
| 2018/0055581 | A1* | 3/2018 | Papac | A61B 34/25 |
| 2019/0189270 | A1* | 6/2019 | Ishii | G16H 50/70 |
| 2020/0251215 | A1* | 8/2020 | Nemoto | G16H 50/20 |
| 2021/0137416 | A1* | 5/2021 | Canfield | G16H 50/30 |

FOREIGN PATENT DOCUMENTS

| | | | | |
|---|---|---|---|---|
| JP | 2015-116331 A | | 6/2015 | |
| JP | 2017-153818 A | | 9/2017 | |
| WO | WO 02/39899 A2 | | 5/2002 | |
| WO | WO2002039899 | * | 5/2002 | ............... A61B 6/00 |
| WO | WO 2019143179 | * | 7/2019 | |
| WO | WO 2019/150715 A1 | | 8/2019 | |

* cited by examiner

FIG. 5

| PROCEDURE | CLASS | SCAN MODE | | | | REFERENCE IMAGE | SET IMAGE | PRIORITY |
|---|---|---|---|---|---|---|---|---|
| | | IMAGE DISPLAY | ANNOTATION SETTING | BODY MARK SETTING | | | | |
| | | RESOLUTION, FRAME RATE, BRIGHTNESS, ⋯ | DETAILS, DISPLAY POSITION, ⋯ | TYPE, DISPLAY POSITION, ⋯ | ⋯ | | | |
| proc_01 | ABDOMEN 1 | ⋯ | ⋯ | ⋯ | ⋯ | p01.bmp | [REFERENCE IMAGE] | |
| proc_02 | | ⋯ | ⋯ | ⋯ | ⋯ | p02.bmp | A.bmp | 1 |
| proc_03 | | ⋯ | ⋯ | ⋯ | ⋯ | p03.bmp | B.bmp | |
| proc_04 | | ⋯ | ⋯ | ⋯ | ⋯ | p04.bmp | [REFERENCE IMAGE] | ⋯ |
| proc_11 | ABDOMEN 2 | ⋯ | ⋯ | ⋯ | ⋯ | p11.bmp | [REFERENCE IMAGE] | ⋯ |
| proc_12 | | ⋯ | ⋯ | ⋯ | ⋯ | p12.bmp | A.bmp | 2 |
| proc_13 | | ⋯ | ⋯ | ⋯ | ⋯ | p13.bmp | C.bmp | ⋯ |
| proc_21 | BREAST | ⋯ | ⋯ | ⋯ | ⋯ | p21.bmp | [REFERENCE IMAGE] | ⋯ |
| proc_22 | | ⋯ | ⋯ | ⋯ | ⋯ | p22.bmp | A.bmp | 3 |
| proc_23 | | ⋯ | ⋯ | ⋯ | ⋯ | p23.bmp | [REFERENCE IMAGE] | ⋯ |
| proc_24 | | ⋯ | ⋯ | ⋯ | ⋯ | p24.bmp | [REFERENCE IMAGE] | ⋯ |
| ⋯ | | | | | | ⋯ | ⋯ | ⋯ |

FIG. 6

| PROTOCOL | EXECUTION ORDER | PROCEDURE | SET IMAGE | PRIORITY |
|---|---|---|---|---|
| protocol_01 | 1 | proc_01 | [REFERENCE IMAGE] | ... |
| | 2 | proc_11 | [REFERENCE IMAGE] | ... |
| | 3 | proc_21 | [REFERENCE IMAGE] | ... |
| | ... | ... | ... | ... |
| protocol_02 | 1 | proc_02 | A.bmp | 1 |
| | 2 | proc_22 | A.bmp | 3 |
| | 3 | proc_12 | A.bmp | 2 |
| | ... | ... | ... | ... |
| protocol_03 | 1 | proc_03 | B.bmp | ... |
| | 2 | proc_13 | C.bmp | ... |
| | 3 | proc_23 | p23.bmp | ... |
| | ... | ... | ... | ... |
| ... | ... | ... | ... | ... | her
ULTRASONIC DIAGNOSTIC DEVICE AND STORAGE MEDIUM

CROSS-REFERENCE TO RELATED APPLICATION

The present application claims priority based on Japanese Patent Application No. 2020-150258 filed Sep. 8, 2020, the content of which is incorporated herein by reference.

BACKGROUND OF THE INVENTION

Field of the Invention

Embodiments disclosed in the present description and drawings relate to an ultrasonic diagnostic device and a storage medium.

Description of Related Art

Conventionally, a medical examination apparatus such as an ultrasonic diagnostic device has an examination supporting function of performing examination according to a procedure registered in advance.

BRIEF DESCRIPTION OF THE DRAWINGS

FIG. 5 is a diagram illustrating an example of procedure information in an embodiment.

FIG. 6 is a diagram illustrating an example of protocol information in an embodiment.

DETAILED DESCRIPTION OF THE INVENTION

Hereinafter, an ultrasonic diagnostic device and a storage medium of embodiments will be described with reference to the drawings.

An ultrasonic diagnostic device of an embodiment includes an image acquisition unit, a control unit, and a determination unit. The image acquisition unit acquires an ultrasonic image of a subject based on an output signal of an ultrasonic probe. The control unit executes processing for each step for each of one or more examination procedures registered in advance and including one or more steps including the processing of acquiring the ultrasonic image, in which set images are associated and registered. The determination unit determines a recommended step recommended to be executed subsequent to a current step or instead of the current step on the basis of a degree of consistency between a set image registered for each of the steps and an ultrasonic image acquired in the current step that is being executed. The control unit executes the recommended step subsequent to the current step or instead of the current step when the recommended step has been determined during execution of the current step.

An ultrasonic diagnostic device of an embodiment includes an image acquisition unit, a control unit, and a determination unit. The image acquisition unit acquires an ultrasonic image of a subject based on an output signal of an ultrasonic probe. The control unit executes processing for each step for each of one or more examination procedures registered in advance and including one or more steps including processing of acquiring the ultrasonic image, in which set images are associated and registered. The determination unit determines a recommended step recommended to be executed subsequent to a current step or instead of the current step on the basis of set images registered in the current step that is being executed and set images set in steps other than the current step. The control unit executes the recommended step subsequent to the current step or instead of the current step when the recommended step has been determined during execution of the current step.

Figure 1:
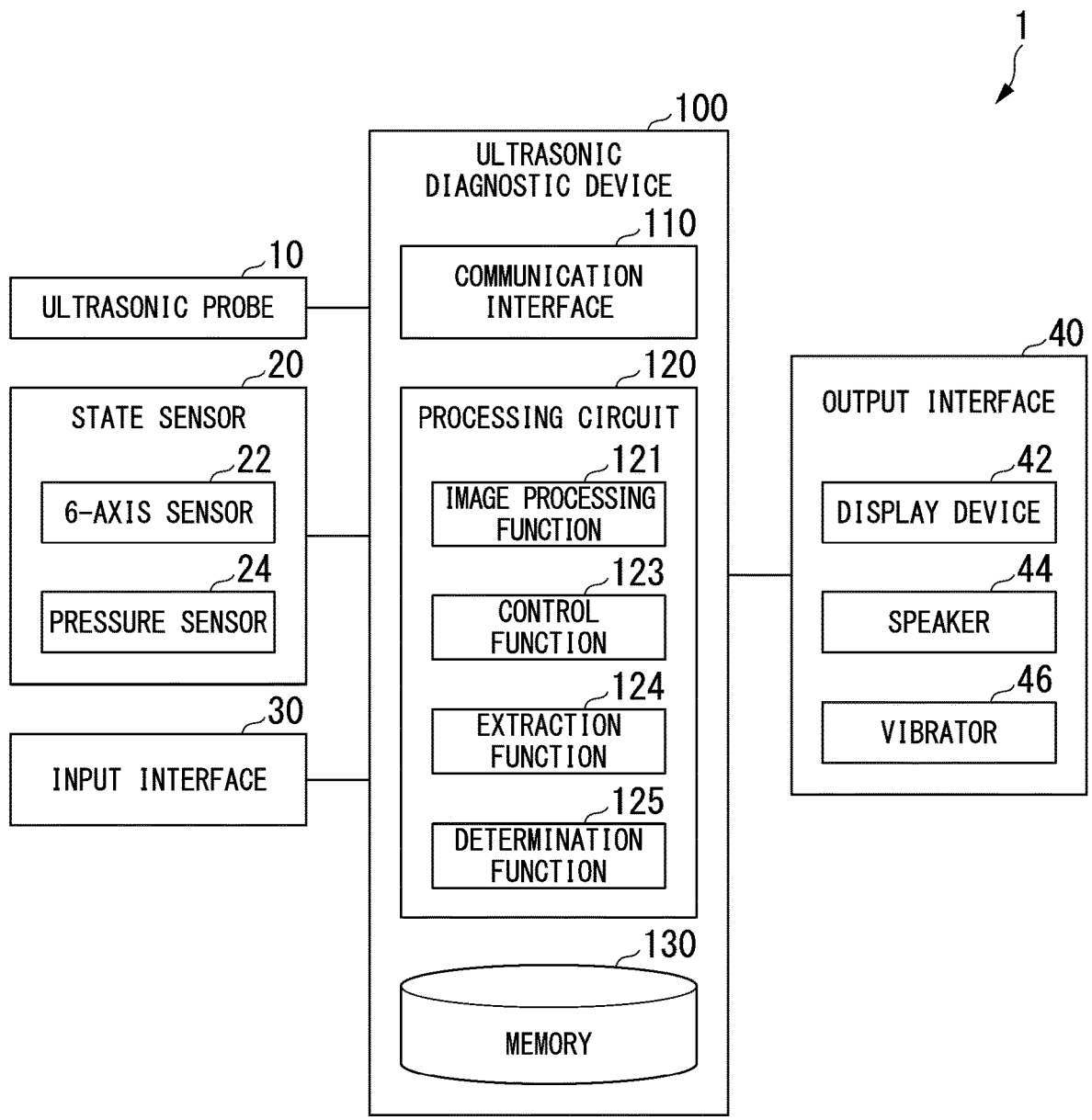
FIG. 1 is a block diagram illustrating an example of a functional configuration of an ultrasonic diagnostic system of an embodiment.

FIG. 1 is a block diagram illustrating an example of a functional configuration of an ultrasonic diagnostic system 1 of an embodiment.

Figure 2:
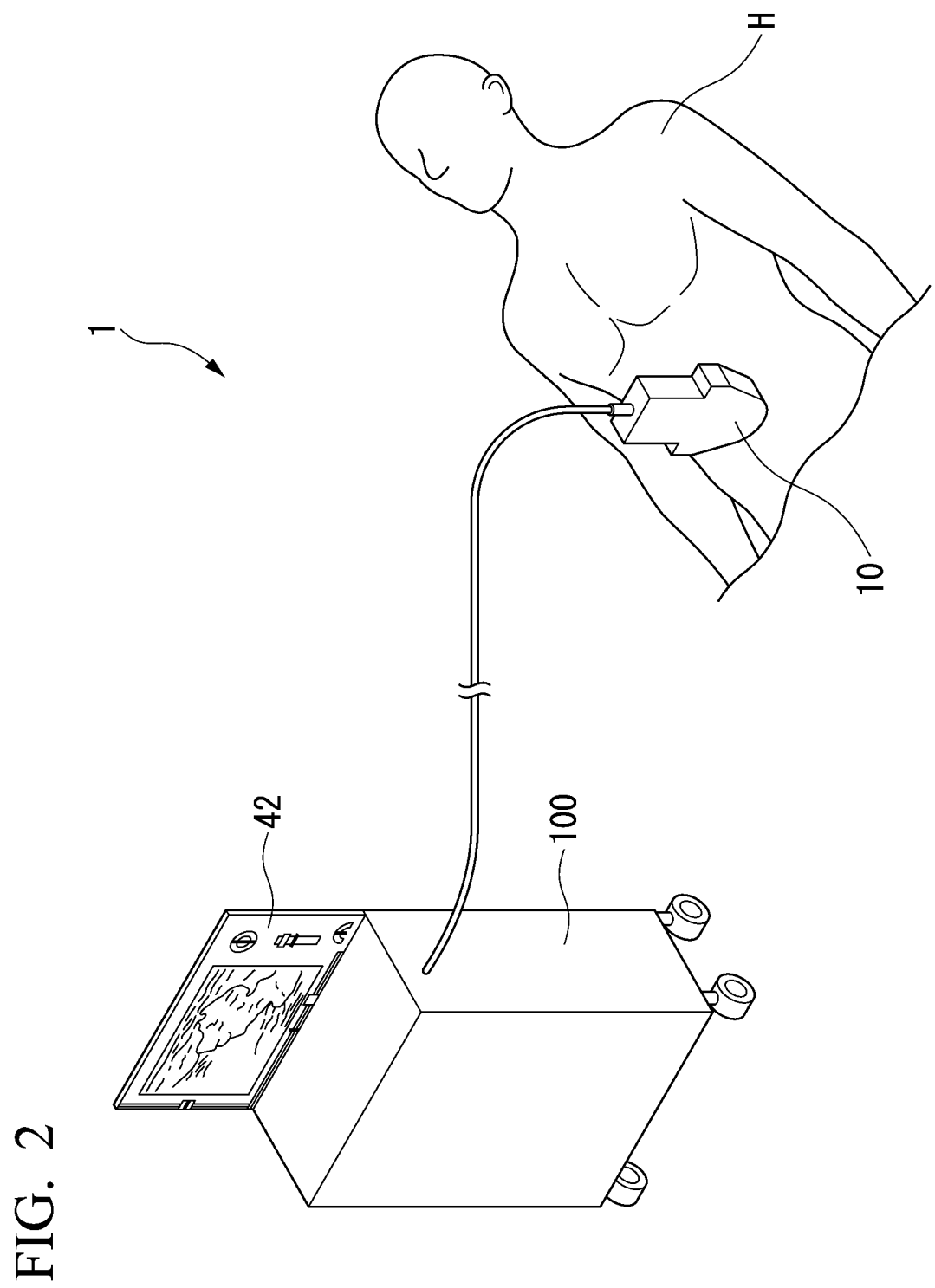
FIG. 2 is a diagram illustrating a situation in which the ultrasonic diagnostic system of the embodiment is used to perform diagnosis on a subject.

In addition, FIG. 2 is a diagram illustrating a situation in which the ultrasonic diagnostic system 1 of the embodiment is used to perform diagnosis on a subject H. As illustrated in FIG. 1, the ultrasonic diagnostic system 1 may include, for example, an ultrasonic probe 10, a state sensor 20, an input interface 30, an output interface 40, and an ultrasonic diagnostic device 100. As illustrated in FIG. 2, a display device 42 is provided in the ultrasonic diagnostic device 100 as one of devices included in the output interface 40.

The ultrasonic probe 10 is pressed to an examination target part of the subject H, for example, on the basis of a manual operation of a user that is not illustrated. For example, the ultrasonic probe 10 may transmit ultrasonic waves to the subject H in order to acquire an image of the inside of the body of the subject H. The ultrasonic probe 10 receives reflected waves of the transmitted ultrasonic waves. The ultrasonic probe 10 generates reflected wave information that is a signal (echo signal) of reflected waves of ultrasonic waves, generated by a transmitting/receiving surface receiving the same, and outputs the reflected wave information to the ultrasonic diagnostic device 100. Although FIG. 1 and FIG. 2 illustrate a configuration in which the ultrasonic diagnostic device 100 includes a single ultrasonic probe 10 for simplification, the ultrasonic diagnostic device 100 may include a plurality of ultrasonic probes 10.

As illustrated in FIG. 1, the state sensor 20 may include, for example, a 6-axis sensor 22 and a pressure sensor 24. The 6-axis sensor 22 and the pressure sensor 24 may be provided, for example, in the ultrasonic probe 10. The state sensor 20 detects a relative position, a scanning direction, a rotation direction, and an inclination with respect to a subject, and a pressure when the ultrasonic probe 10 is pressed to the subject (hereinafter referred to as a "pressing pressure") as states of the ultrasonic probe 10 with respect to the subject. The state of the ultrasonic probe 10 with respect to the subject may be detected by a sensor other than the state sensor 20.

The 6-axis sensor 22 may be, for example, a sensor that detects 3-axis accelerations and 3-axis angular speeds. The 6-axis sensor 22 detects a relative position, a scanning direction, a scanning speed, a rotation direction (rotation speed), and an inclination (direction) of the ultrasonic probe 10 with respect to the subject on the basis of detected 3-axis accelerations and 3-axis angular speeds. For example, the 6-axis sensor 22 may detect an acceleration in each direction in three dimensions and calculate a difference between a known position (e.g., a default position) and a current position. The 6-axis sensor 22 detects a relative position and a scanning direction of the ultrasonic probe 10 with respect to the subject on the basis of the calculated position difference. To detect the relative position and the scanning direction, a 3-axis sensor may be included instead of the 6-axis sensor 22.

The relative position of the ultrasonic probe 10 with respect to the subject may be detected through other methods.

For example, a relative position sensor may include a camera that captures the subject. In this case, the relative position sensor may detect the relative position of the ultrasonic probe 10 with respect to the subject, for example, according to optical difference identification using an image captured by the camera. The relative position sensor may be a sensor using an electromagnetic method.

The 6-axis sensor 22 may detect a current position of the ultrasonic probe 10, for example, on the basis of 3-axis accelerations. The 6-axis sensor 22 may calculate a scanning direction of the ultrasonic probe 10, for example, by calculating the difference between the current position of the ultrasonic probe 10 and a known position (e.g., a default position). The 6-axis sensor 22 may calculate a scanning speed of the ultrasonic probe 10, for example, on the basis of a rate of change in the scanning direction of the ultrasonic probe 10. The scanning direction and the scanning speed of the ultrasonic probe 10 may be obtained by a 3-axis sensor that detects 3-axis accelerations.

The 6-axis sensor 22 may detect a rotation direction of the ultrasonic probe 10, for example, on the basis of 3-axis angular speeds. The 6-axis sensor 22 may calculate the rotation direction of the ultrasonic probe 10, for example, by calculating the difference between a current angle of the ultrasonic probe 10 and a known angle (e.g., a default angle). The 6-axis sensor 22 may calculate the rotation speed of the ultrasonic probe 10, for example, on the basis of the rate of change in the rotation direction of the ultrasonic probe 10. The 6-axis sensor 22 outputs information on the relative position, the scanning direction, the scanning speed, the rotation direction (rotation speed), and an inclination (direction) which are detected states of the ultrasonic probe 10 with respect to the subject to the ultrasonic diagnostic device 100.

The pressure sensor 24 may be formed, for example, from a conductive film including a piezoelectric layer on the inner side thereof. The pressure sensor 24 may include, for example, two outer electrodes on the outer side thereof and an inner electrode sandwiched between the two outer electrodes. When a pressure is applied between the two electrodes on the outer side, the pressure sensor 24 measures the current value of a current flowing between the electrodes. The pressure sensor 24 detects a pressure applied to the pressure sensor 24, in other words, the pressure applied between the subject and the ultrasonic probe 10, on the basis of the measured current value. The pressure sensor 24 outputs information on the detected pressure to the ultrasonic diagnostic device 100. In the following description, information on the state of the ultrasonic probe 10 with respect to the subject is referred to as "probe state information."

The 6-axis sensor 22 may detect 3-axis accelerations and 3-axis angular speeds of the ultrasonic probe 10. The pressure sensor 24 may detect a measured current value. In this case, the state sensor 20 outputs the 3-axis accelerations and the 3-axis angular speeds of the ultrasonic probe 10, detected by the 6-axis sensor 22 and detection information of the current value measured by the pressure sensor 24 to the ultrasonic diagnostic device 100. The ultrasonic diagnostic device 100 calculates probe state information on the basis of the output detection information.

The input interface 30 may include, for example, physical operation parts such as a mouse, a keyboard, and a touch panel. The input interface 30 may output, for example, subject information such as details stored in a hospital system (hospital information system (HIS)) and details written on a medical questionnaire to the ultrasonic diagnostic device 100 according to user operation or the like. For example, the hospital information system may be a system for improving efficiency of medical examination and accounting work of a hospital in which the ultrasonic diagnostic device 100 is installed and may store subject information. A medical questionnaire stores subject information in order to collect information related to examinations when a subject receives a medical checkup. A medical questionnaire may be written on paper or may be stored in an electronic medium. The input interface 30 may be an optical character recognition (OCR) system in consideration of a case in which a medical questionnaire is on paper.

Subject information may be obtained from an ordering system, a radiology information system (RIS), an electronic medical chart system, and the like, which correspond to the hospital information system and have examination information, instead of the hospital information system. Subject information may be used, for example, to obtain an operation candidate for the ultrasonic probe 10. When subject information is information based on a hospital system, the subject information may include information such as an examination purpose, an examination part, and an execution protocol, provided by the hospital system.

Subject information stored in a hospital system may include, for example, items indicating subject characteristics such as "examination purpose," "examination part." "execution protocol." Subject information written on a medical questionnaire may include, for example, items such as "height," "weight." "BMI," "blood pressure," "body fat," "sex." "age," "medical history," "ethnicity (race)," "occupation." "diet," "drinking habits," "smoking history," "exercise habits," "family medical history", and in the case of a female subject, "history of giving birth." "menarcheal age," "menopausal age," "menstruation state," and "lactation period"

The aforementioned execution protocol is an examination execution procedure (examination procedure) performed using various examination devices and diagnostic devices in order to perform diagnosis on a subject. The execution protocol is created in response to an examination purpose, an examination part, and the like and represented by a combination of one or more steps. Information about such an execution protocol is registered in the ultrasonic diagnostic device 100 of the embodiment in advance. The ultrasonic diagnostic device 100 supports a diagnostic operation of a user (e.g., a doctor, an examination engineer, or the like) by performing an operation based on the execution protocol.

Processing executed by the ultrasonic diagnostic device 100 on the basis of an execution protocol will be simply referred to as a "protocol" hereinafter for simplification. In addition, processing corresponding to an operation of each step included in an execution protocol will be referred to as a "procedure."

Further, the input interface 30 is not limited to a unit including physical operation parts such as a mouse and a keyboard in the present description. For example, an electrical signal processing circuit that receives an electrical signal corresponding to an input operation from an external input apparatus provided separately from the device and outputs the electrical signal to a control circuit may also be included in examples of the input interface 30. The output interface 40 may be provided in the ultrasonic diagnostic device 100 or may be provided separately from the ultrasonic diagnostic device 100.

The output interface 40 may include, for example, the display device 42, a speaker 44, a vibrator 46, and the like. The display device 42 may be disposed, for example, at a position at which an image that can be visually recognized by a user is displayed. The display device 42 displays an image based on information output from the ultrasonic diagnostic device 100. The display device 42 presents operation candidates for the ultrasonic probe 10 through the vision of a user or the like. The display device 42 may be, for example, a display or a projector that projects an image.

The speaker 44 may be disposed, for example, at a position at which a user can hear vocal sound. The speaker 44 outputs vocal sound based on information output from the ultrasonic diagnostic device 100. The speaker 44 presents operation candidates for the ultrasonic probe 10 for the hearing of a user or the like. The speaker 44 may present operation candidates for the ultrasonic probe 10, for example, according to an intensity of vocal sound, a length of an interval, a pitch, and the like. The speaker 44 may be provided, for example, in a headphone or an earphone worn by a user. The vibrator 46 may be provided, for example, at a position at which a user can sense vibration. For example, the vibrator 46 may be used by being put on the body of a user or being put in the clothes of the user. The vibrator 46 vibrates in response to information output from the ultrasonic diagnostic device 100. The vibrator 46 presents operation candidates for the ultrasonic probe 10 through the tactile sensation of a user or the like. When operation candidates for the ultrasonic probe 10 are presented through the tactile sensation, for example, a method of adjusting a pressure resistance difference from a subject through the ultrasonic probe 10, and the like may be used.

Subsequently, a configuration of the ultrasonic diagnostic device 100 will be described. The ultrasonic diagnostic device 100 may include, for example, a communication interface 110, a processing circuit 120, and a memory 130.

The processing circuit 120 may include, for example, an image acquisition function 121, a control function 123, an extraction function 124, and a determination function 125. The processing circuit 120 may realize these functions, for example, by a hardware processor executing a program stored in a memory 130.

The hardware processor may mean, for example, a circuit (circuitry) such as a central processing unit (CPU), a graphics processing unit (GPU), an application specific integrated circuit (ASIC), a programmable logic device (e.g., a simple programmable logic device (SPLD) or a complex programmable logic device (CPLD)), or a field programmable gate array (FPGA). The program may be directly incorporated in the circuit of the hardware processor instead of being stored in the memory 130. In this case, the hardware processor realizes functions by reading and executing the program incorporated in the circuit. The hardware processor is not limited to a configuration as a single circuit and may be configured as a single hardware processor by combining a plurality of independent circuits to realize respective functions. In addition, the respective functions may be realized by a single hardware processor in which a plurality of components are integrated. The memory 130 may be a non-transitory (hardware) storage medium. The memory 130 stores device information representing device characteristics of the host device, such as the type, model number, specification, installation date, and production date of the ultrasonic diagnostic device 100, as part of existing data.

The communication interface 110 may include, for example, a communication interface such as a network interface card (NIC). The communication interface performs communication of information between the ultrasonic probe 10, the state sensor 20, the input interface 30, and the output interface 40 in a wired manner or through a network. The communication interface 110 outputs received information to the processing circuit 120. In addition, the communication interface 110 may be controlled by the processing circuit 120 such that it transmits information to other devices connected in a wired manner or through a network.

The communication interface 110 receives reflected wave information transmitted from the ultrasonic probe 10. The communication interface 110 receives probe state information output from the state sensor 20. The communication interface 110 transmits guide information generated by the processing circuit 120 to the output interface 40.

The image acquisition function 121 converts reflected wave information output from the ultrasonic probe 10 into image information and generates an ultrasonic image that is an image representing a state inside the body of a subject. The image acquisition function 121 stores the generated ultrasonic image in the memory 130. The image acquisition function 121 is an example of an "image acquisition unit."

The control function 123 causes a device including the communication interface 110, the processing circuit 120, and the memory 130 to serve as an ultrasonic diagnostic device operating in connection with the ultrasonic probe 10, the state sensor 20, the input interface 30, and the output interface 40 by executing various types of control processing.

For example, the control function 123 may execute a protocol selected by a user among one or more protocols registered in the ultrasonic diagnostic device 100. For example, the control function 123 may execute procedures included in the selected protocol in a predetermined order while timely performing input/output of necessary information between the input interface 30 and the output interface 40.

For example, the control function 123 obtains ultrasonic images acquired during execution of procedures from the memory 130, reproduces the acquired ultrasonic images in the order in which they have been generated and causes the display device 42 to display the ultrasonic images. The control function 123 may temporarily stop reproduction of ultrasonic images or change a reproduction speed. According to reproduction and display of such ultrasonic images, a user can perform diagnosis on the health condition of a subject or search for a lesion. Further, the control function 123 may directly receive an ultrasonic image output from the image acquisition function 121 and cause the display device 42 to display the ultrasonic image. In this case, the control function 123 may record the received ultrasonic image in the memory 130 or the like as necessary or perform recording of the ultrasonic image.

Figure 3:
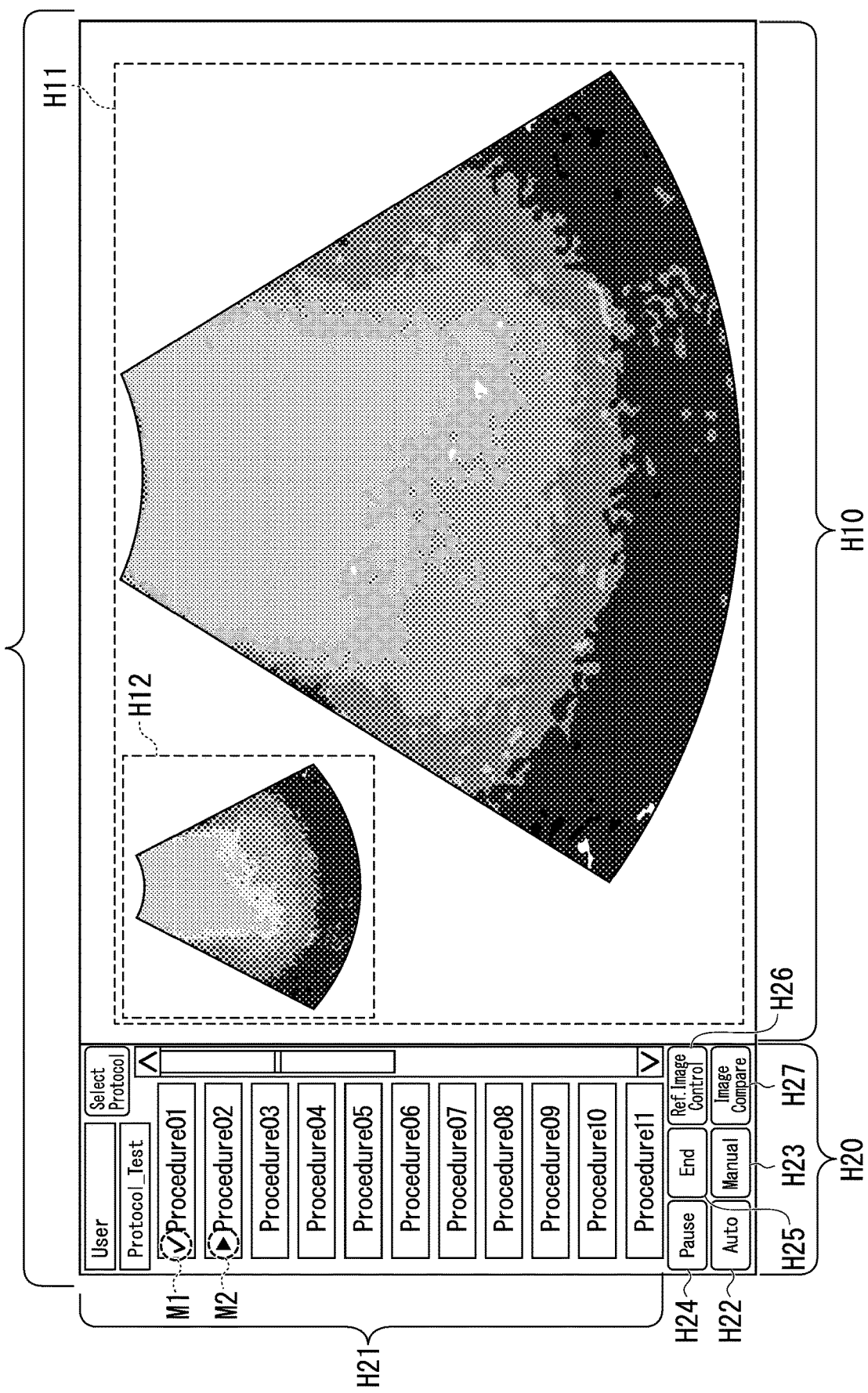
FIG. 3 is a diagram illustrating an example of a diagnostic screen displayed on a display device of an embodiment.

FIG. 3 is a diagram illustrating an example of a screen (hereinafter referred to as a "diagnostic screen") displayed on the display device 42 during execution of a protocol. For example, a diagnostic screen may include a display area H10 in which an ultrasonic image acquired during execution of a protocol is displayed and an operation area H20 through which an operation input with respect to the protocol that is being executed is received like a diagnostic screen H illustrated in FIG. 3.

For example, an ultrasonic image H11 acquired from the ultrasonic probe 10 that is being operated and a reference image H12 registered in association with a procedure that is being executed may be displayed in the display area H10. For example, the reference image H12 displayed in FIG. 3 may be an image showing an example of an ultrasonic image expected to be acquired in the procedure that is being executed. Such a reference image is displayed simultaneously with an actually acquired ultrasonic image, and thus a user can operate the ultrasonic probe 10 using the reference image as a model to perform a diagnosis with high efficiency. Further, in addition to such an image, any image may be used as a reference image as long as it aims at supporting an operation of a user with respect to a procedure that is being executed. For example, an illustration of an examination target part, a note on which precautions and the like at the time of a diagnosis are recorded, and the like may be displayed as reference images.

In addition, user interfaces H22 to H27 for calling a predetermined function with respect to execution of a protocol may be displayed in the operation area H20 in addition to a user interface H21 with respect to procedures included in the protocol that is being executed, for example. For example, a user can select a procedure and instruct the selected procedure to be executed by operating H21. H21 may be configured to represent an execution state and attributes of each procedure according to a display mode thereof. For example, H21 illustrated in FIG. 3 is an example of a user interface configured to represent a completion status of a procedure according to the presence or absence of a check mark M1 and to indicate a procedure that is being executed according to a triangular mark M2.

In addition, the user can change an operation mode of the ultrasonic diagnostic device 100 with respect to execution of a procedure by operating H22 and H23, for example. In the present embodiment, the ultrasonic diagnostic device 100 can operate in "automatic mode" or "manual mode." The automatic mode is an operation mode in which the ultrasonic diagnostic device 100 automatically selects a procedure that is an execution target from a plurality of procedures and executes the selected procedure. The manual mode is an operation mode in which the ultrasonic diagnostic device 100 executes a procedure that is an execution target according to selection and execution instruction of a user. For example, H22 may be a user interface for selecting "automatic mode" ("Auto") and H23 may be a user interface for selecting "manual mode" ("Manual").

In addition, the user can temporarily stop renewal of display of an ultrasonic image that is being acquired and cancel temporary stop, for example, by operating H24. Further, the user can input end of an operation with respect to a procedure that is being executed, for example, by operating H25. In addition, the user can change settings (a display target image, a display position, a display size, and the like) with respect to a reference image, for example, by operating H26. Further, the user can compare a reference image with an ultrasonic image, for example, by operating H27.

In addition, when a procedure (hereinafter referred to as a "recommended procedure") recommended to be executed following a procedure that is being executed (hereinafter referred to as a "current procedure") is determined, for example, the control function 123 changes an execution target procedure from the current procedure to the recommended procedure. Here, "following a procedure that is being executed" includes not only a case in which an execution target procedure is changed upon completion of the current procedure but also a case in which the execution target procedure is changed before completion of the current procedure. For example, in the case of the automatic mode, the control function 123 can change an execution target procedure to a recommended procedure even when the current procedure is not completed if execution initiation conditions for the recommended procedure are satisfied. Further, in the case of the manual mode, for example, the control function 123 can change an execution target procedure to a recommended procedure when the user inputs completion of the current procedure and instructs the recommended procedure to be executed.

The extraction function 124 extracts procedures that are candidates for recommended procedures (hereinafter referred to as "candidate procedures") from procedures registered in the ultrasonic diagnostic device 100 on the basis of an ultrasonic image acquired in the current procedure. For example, the extraction function 124 may calculate a degree of consistency between an image for comparison (hereinafter referred to as "set image") set in each procedure in advance and an ultrasonic image and extract procedures having degrees of consistency equal to or greater than a threshold value as candidate procedures. The extraction function 124 notifies the determination function 125 of the extracted candidate procedures.

The determination function 125 determines a recommended procedure among the candidate procedures notified of by the extraction function 124. When a single candidate procedure has been notified of by the extraction function 124, the determination function 125 determines the candidate procedure as a recommended procedure.

In addition, when a plurality of candidate procedures have been notified by the extraction function 124, the determination function 125 determines any one of the plurality of candidate procedures as a recommended procedure. A method of determining a recommended procedure among candidate procedures will be described later.

The memory 130 may be realized, for example, by a semiconductor memory element such as a random access memory (RAM) or a flash memory, a hard disk, and an optical disk. These non-transitory storage media may be realized by other storage devices connected through a communication network NW such as a network attached storage (NAS) and an external storage server device. In addition, the memory 130 may include non-transitory storage media such as a read only memory (ROM) and a register. The memory 130 may store, for example, information such as setting information of protocols (hereinafter referred to as "protocol information"), setting information of procedures (hereinafter referred to as "procedure information"), ultrasonic images acquired through each procedure, and reference images and set images set in each procedure. In addition, the memory 130 stores programs, parameter data, and other data used by the processing circuit 120. Details of anonymization recommendation degree reference data 201, threshold value reference data 203, and standard data 205 will be described later.

Figure 4:
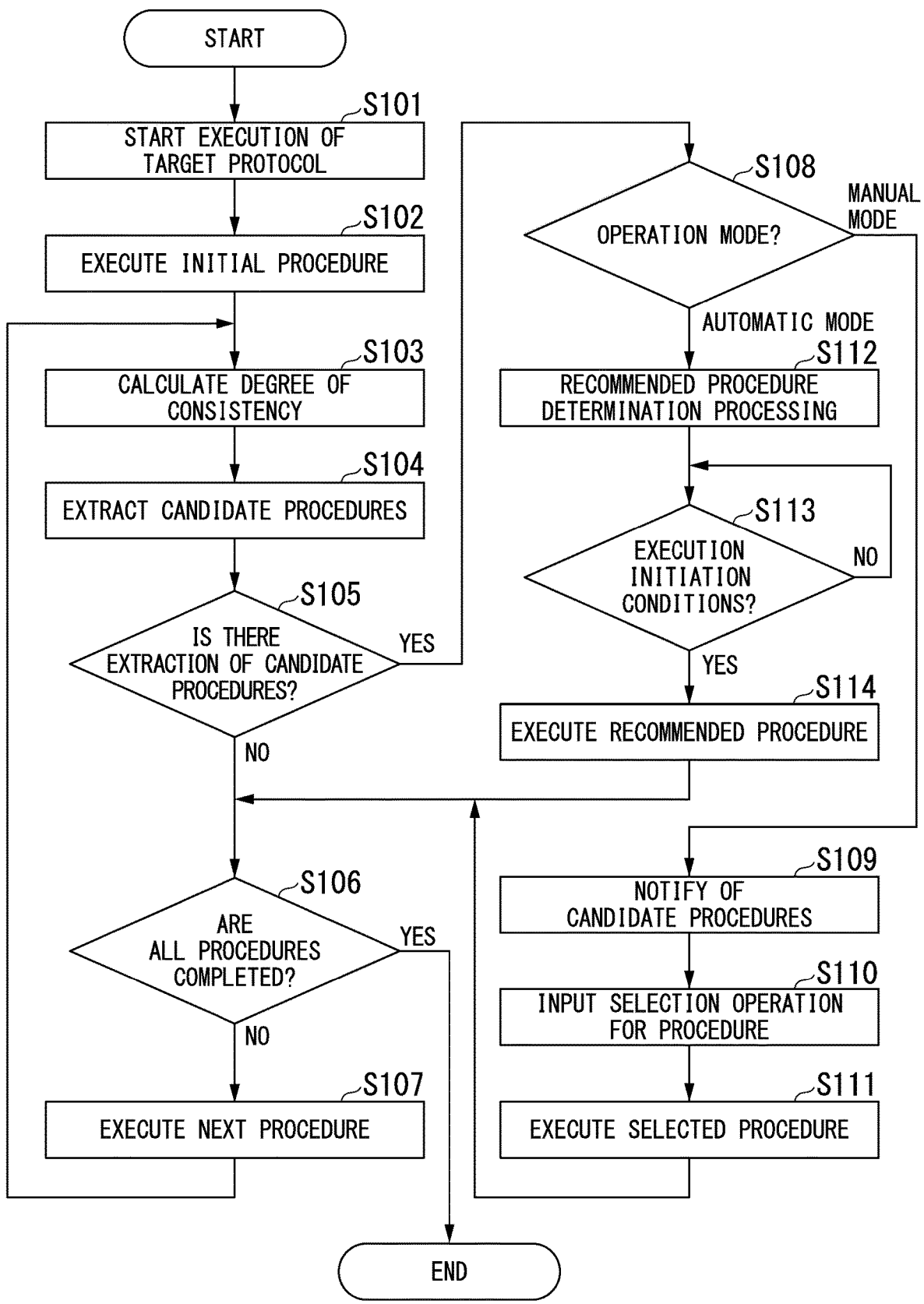
FIG. 4 is a flowchart illustrating an example of processing for controlling execution of a protocol by an ultrasonic diagnostic device of an embodiment.

FIG. 4 is a flowchart illustrating an example of processing for controlling execution of a protocol by the ultrasonic diagnostic device 100 of the embodiment. First, the control function 123 acquires protocol information on an execution target protocol (hereinafter referred to as a "target protocol") from the memory 130 and starts execution of the target protocol on the basis of the acquired protocol information (step S101). Here, it is assumed that the target protocol has been designated in advance by a user. Subsequently, the control function 123 executes an initial procedure in the target procedure (step S102). For example, it is assumed that the initial procedure has been set in advance in the protocol information or is designated by the user at the time of starting execution of the target protocol.

Subsequently, the extraction function 124 acquires a set image set in the current procedure from the memory 130 and calculates a degree of consistency between the acquired set image and an ultrasonic image acquired in the current procedure (step S103). Here, to calculate a degree of consistency, an existing technology such as a method based on local feature amounts, a method based on a histogram of each pixel value, a method based on an average of pixel values, a method using a trained model generated according to machine learning such as a neural network or deep learning, or the like may be used.

The extraction function 124 attempts to extract candidate procedures from procedures registered in the ultrasonic diagnostic device 100 on the basis of the calculated degree of consistency (step S104). The extraction function 124 determines whether candidate procedures have been extracted in step S104 (step S105). For example, the extraction function 124 may extract, as candidate procedures, procedures which have been registered in the ultrasonic diagnostic device 100 and have degrees of consistency equal to or greater than a threshold value among procedures other than procedures that are completed in the current protocol.

Although not illustrated in FIG. 4, the control function 123 is assumed to appropriately manage a completion status of a procedure. For example, the control function 123 can receive input of an operation of representing that a procedure is completed during execution of the procedure and detect completion of the procedure that is being executed upon input of the operation in the manual mode. In addition, the control function 123 may determine that a procedure is completed when it is determined that an ultrasonic image expected with respect to the procedure has been acquired during execution of the procedure in the automatic mode, for example. Further, the control function 123 can change a completion status of a procedure in response to input of an operation of canceling completion of the procedure, for example.

If it is determined that candidate procedures have not been extracted in step S105 (NO in step S105), the control function 123 determines whether all procedures of the protocol that is being executed are completed (step S106). Here, if it is determined that all procedures of the protocol that is being executed are completed (YES in step S106), the control function 123 ends a series of multiple steps of processing. On the other hand, if it is determined that some procedures included in the protocol that is being executed are not completed (NO in step S106), the control function 123 selects a procedure to be executed next from the procedures that are not completed, executes the selected procedure (step S107), returns processing to step S103, and repeatedly executes processing of step S103 and following processing until all procedures are completed.

FIG. 5 is a diagram illustrating an example of procedure information in the present embodiment. In addition, FIG. 6 is a diagram illustrating an example of protocol information in the present embodiment. For example, procedure information may be kept in the memory 130 as a table in which procedure identification information, a procedure type, a scan mode of a procedure, reference images, set images, and priority of the set images are associated. Here, the scan mode is a procedure execution condition and may be represented, for example, by conditions such as image display, annotation, and a body mark. In FIG. 5, "[reference image]" represents that a reference image is set as a set image.

In addition, protocol information is kept in the memory 130 as a table in which protocol identification information, identification information of procedures constituting a protocol, procedure execution order, set images of each procedure, and priority of set images are associated, for example. Procedures, set images, and priority shown in FIG. 6 correspond to procedures, set images, and priority shown in FIG. 5.

For example, in a case in which protocol information and procedure information are set as in FIG. 5 and FIG. 6, when a target protocol is protocol_01 and a current procedure is proc_01, the extraction function 124 calculates degrees of consistency between an ultrasonic image acquired during execution of proc_01 and set images of procedures other than proc_01 that is being executed and extracts procedures having degrees of consistency equal to or greater than the threshold value as candidate procedures.

Here, a target procedure (hereinafter referred to as an "extraction target procedure") attempted to be extracted as a candidate procedure may not be at least the current procedure and a procedure that is completed in a target protocol among procedures registered in the ultrasonic diagnostic device 100, but it may be limited to a procedure that satisfies further conditions as necessary. For example, an extraction target procedure may be limited to a procedure included in a target protocol or limited to a procedure included in a protocol that is not being executed.

Furthermore, an extraction target procedure may be limited to a procedure that is not included in any protocol or limited to a procedure managed according to different classification (for example, "type" in FIG. 5, and the like) from protocols, for example.

The extraction function 124 curbs a procedure that has already been completed from being included in candidate procedures by excluding completed procedures from extraction target procedures. In addition, when an operation of canceling completion of a procedure is input, the extraction function 124 adds the procedure to extraction target procedures again such that the user can resume a procedure as necessary.

Referring back to FIG. 4, when it is determined that the candidate procedures have been extracted in step S105 (YES in step S105), the extraction function 124 notifies the determination function 125 of the extracted candidate procedures. Upon reception of this notification, the determination function 125 determines whether a current operation mode is either of the automatic mode or the manual mode (step S108). It is assumed that the ultrasonic diagnostic device 100 appropriately receives input of an operation of changing operation modes and a user can change the operation mode as necessary. Here, when it is determined that the current operation mode is the manual mode (step S108: manual mode), the determination function 125 notifies the user of the notified candidate procedures (step S109).

For example, the determination function 125 may cause the display device 42 to display the candidate procedures.

Figure 7:
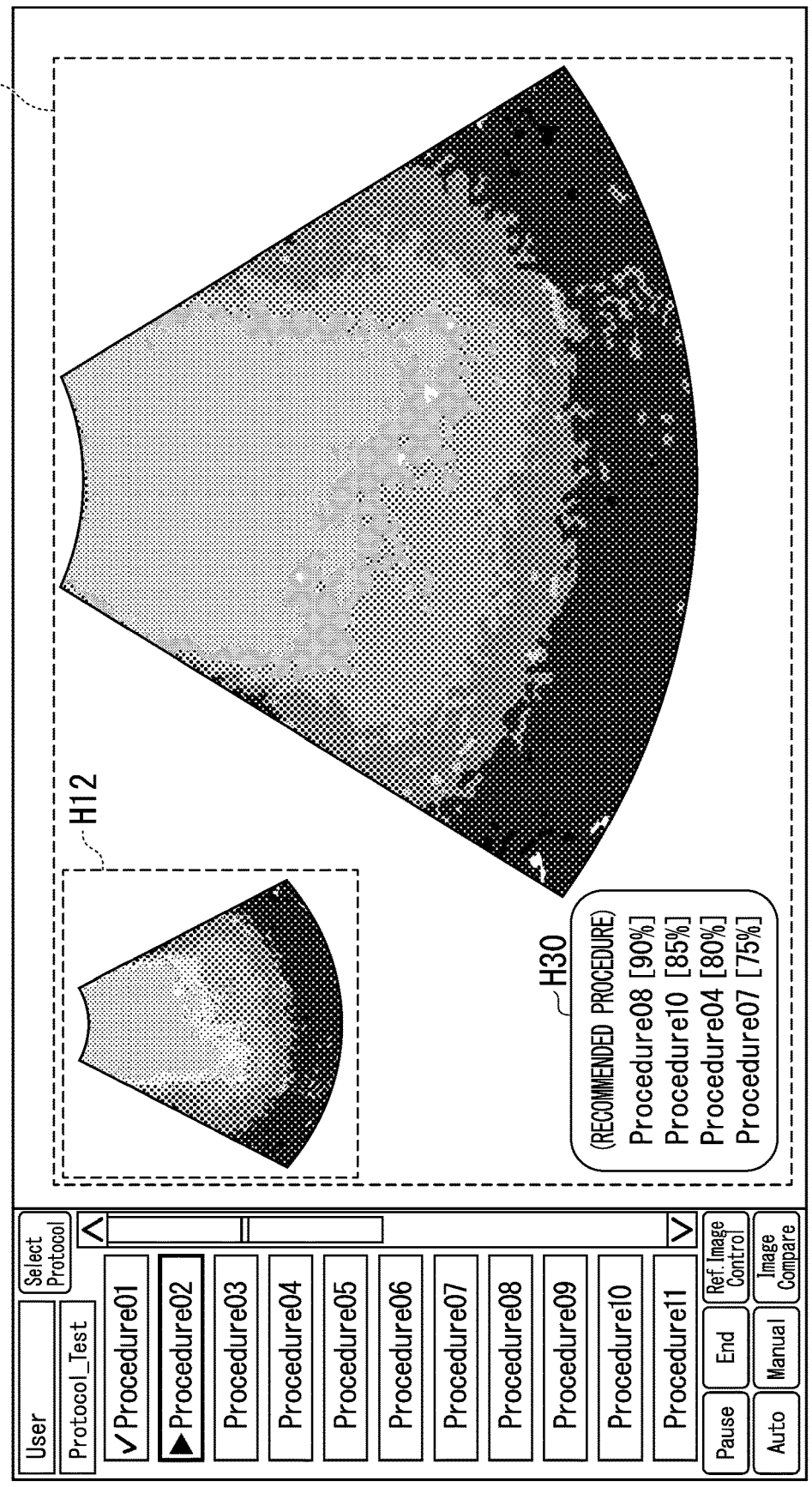
FIG. 7 is a diagram illustrating a display example of a candidate procedure in an embodiment.

FIG. 7 is a diagram illustrating a display example of candidate procedures in the present embodiment. For example, FIG. 7 illustrates an example in which four candidate procedures are extracted during execution of Procedure02 that is the current procedure and a pop-up H30 notifying the candidate procedures is displayed in front of an ultrasonic image H11. In this example, the four candidate procedures are listed in descending order of degrees of consistency and a degree of consistency of each procedure is indicated in [ ] in the pop-up H30.

Referring back to FIG. 4, subsequently, the determination function 125 receives input of an operation of selecting a procedure (step S110). Here, the selecting operation may be an operation of selecting any one of procedures that are not completed among procedures included in the target protocol or an operation of selecting any one of the displayed candidate procedures. When the operation of selecting a procedure is input, the determination function 125 notifies the control function 123 of the selected procedure. Upon reception of this notification, the control function 123 executes the procedure notified of by the determination function 125 (step S111). In this manner, a recommended procedure is selected from the candidate procedures according to user operation in the manual mode.

On the other hand, when it is determined that the current operation mode is the automatic mode in step S108 (step S108: automatic mode), the determination function 125 determines a recommended procedure among the extracted candidate procedures by executing recommended procedure determination processing (step S112) and notifies the control function 123 of the determined recommended procedure. Upon reception of this notification, the control function 123 determines whether execution initiation conditions are satisfied with respect to the notified recommended procedure (step S113). For example, the control function 123 may determine the following conditions as execution initiation conditions.

[Execution Initiation Conditions for Recommended Procedure]

(1-1) An ultrasonic image acquired in a procedure that is being executed represents a part clearly different from an expected part. For example, this condition can be determined on the basis of a degree of consistency between the acquired ultrasonic image and a set image of the procedure that is being executed. In this case, a degree of consistency may be acquired by the extraction function 124 or may be calculated by the control function 123 through the same method as the extraction function 124.

(1-2) A state in which a motion of a subject is large continues for a certain time in an ultrasonic image acquired in a procedure that is being executed (that is, a time in which a part to be captured is searched is long). For example, this condition can be determined on the basis of the size of the difference between frames of the acquired ultrasonic image.

(1-3) A certain time has elapsed after a procedure that is being executed ends.

When it is determined that the execution initiation conditions for the recommended procedure are satisfied in step S113 (YES in step S113), the control function 123 executes the recommended procedure (step S114) and then proceeds with processing to step S106. On the other hand, when it is determined that the execution initiation conditions for the recommended procedure are not satisfied (NO in step S113), the control function 123, the control function 123 repeatedly executes step S113 until the execution initiation conditions are satisfied. Here, when the execution initiation conditions are not satisfied even when execution of step S113 is repeated a predetermined number of times, the control function 123 may proceed with processing to step S106 on the assumption that candidate procedures are not extracted in step S105 (NO in step S105).

The control function 123 may be configured to perform the following operations when it is estimated that the recommended procedure executed in the automatic mode is not a procedure expected by the user (for example, a case in which the user has input an operation representing it, a case in which the ultrasonic probe 10 is not operated for a certain time or longer, and the like).

(3-1) The automatic mode is changed to the manual mode and a user interface for causing a user to select a procedure to be executed instead of a recommended procedure that is being executed is provided.

(3-2) A user interface for selecting a procedure to be executed instead of a recommended procedure that is being executed from other candidate procedures extracted along with the recommended procedure that is being executed is provided.

(3-3) A new recommended procedure is determined on the basis of a degree of consistency with an ultrasonic image acquired by a recommended procedure that is being executed and executed.

(3-4) A recommended procedure that is being executed is changed to a former procedure that has been executed before the recommended procedure or a user interface for changing the recommended procedure to the former procedure is provided.

(3-5) A recommended procedure that is being executed is changed to a procedure with a high degree of consistency or high priority second to the recommended procedure among other candidate procedures extracted along with the recommended procedure.

Figure 8:
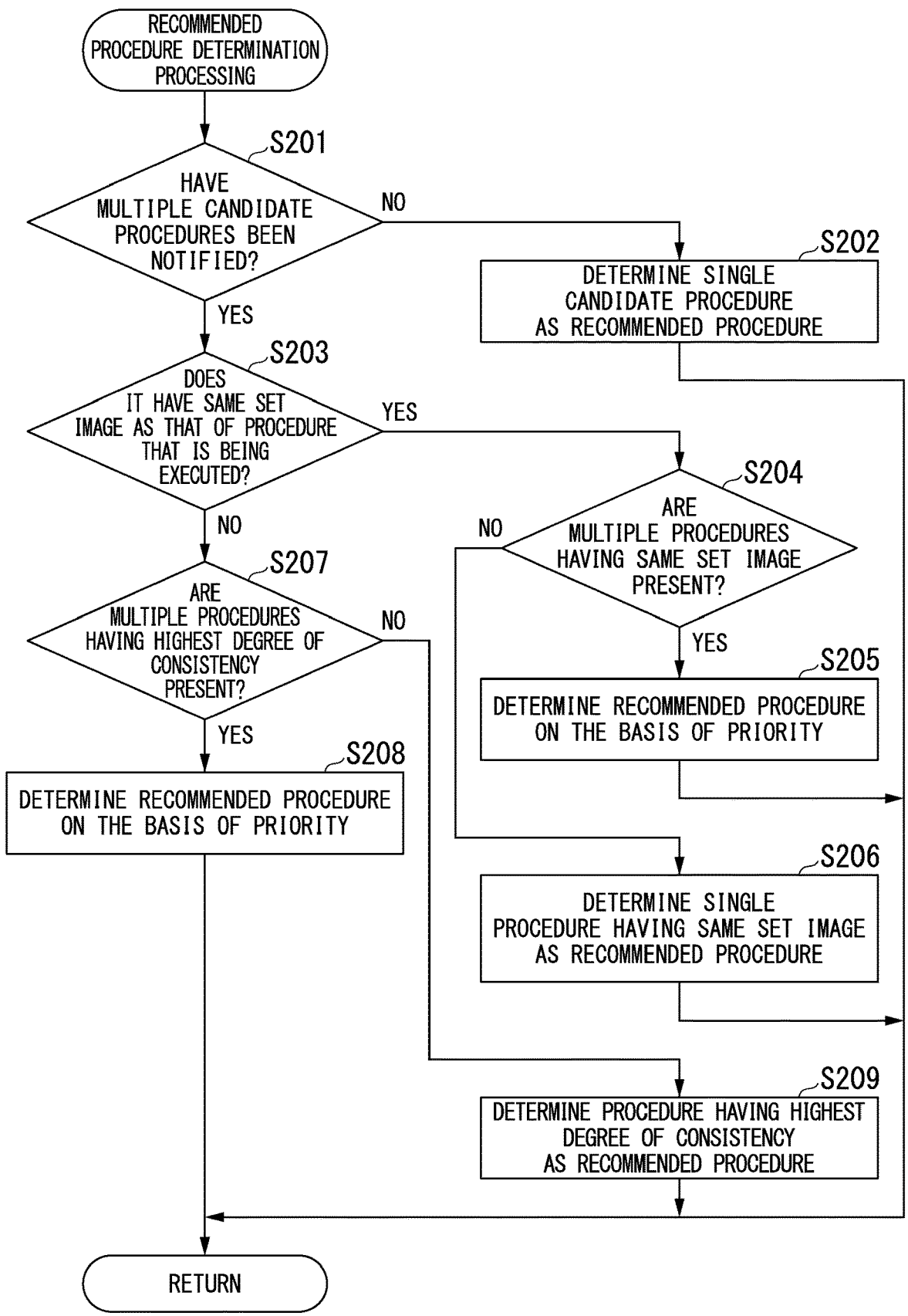
FIG. 8 is a flowchart illustrating an example of recommended procedure determination processing in an embodiment.

FIG. 8 is a flowchart illustrating an example of recommended procedure determination processing in an embodiment. First, the determination function 125 determines whether a plurality of candidate procedures have been notified of by the extraction function 124 (step S201). Here, when it is determined that a single candidate procedure has been notified (NO in step S201), the determination function 125 determines the notified single candidate procedure as a recommended procedure (step S202) and ends the recommended procedure determination processing.

On the other hand, when it is determined that a plurality of candidate procedures have been notified in step S201 (YES in step S201), the determination function 125 determines whether the plurality of candidate procedures include a procedure having the same set image as that of a procedure that is being executed (step S203). Here, when it is determined that the plurality of candidate procedures include a procedure having the same set image as that of the procedure that is being executed (YES in step S203), the determination function 125 determines whether a plurality of procedures having the same set image are present (step S204). Here, when it is determined that a plurality of procedures having the same set image are present (YES in step S204), the determination function 125 determines a recommended procedure on the basis of the priority of the set image (step S205) and ends the recommended procedure determination processing.

For example, in the example of the procedure information and the protocol information shown in FIG. 5 and FIG. 6, a case in which the extraction function 124 extracts proc_22, proc_12, and proc_03 as candidate procedures when a protocol that is being executed is protocol_02 and a procedure that is being executed is proc_02 may be conceived. In this case, since a set image of the procedure proc_02 that is being executed is A.bmp, the determination function 125 determines proc_12 having higher priority between proc_22 and proc_12 having the same set image as a recommended procedure.

On the other hand, when it is determined that a plurality of procedures having the same set image are not present in step S204 (NO in step S204), that is, when the candidate procedures include only a single procedure having the same set image as that of the procedure that is being executed, the determination function 125 determines the procedure having the same set image as a recommended procedure (step S206).

On the other hand, when it is determined that the plurality of candidate procedures do not include a procedure having the same set image as that of the procedure that is being executed in step S203 (NO in step S203), the determination function 125 determines whether the candidate procedures include a plurality of procedures having the highest degree of consistency (step S207). Here, when it is determined that the candidate procedures include a plurality of procedures having the highest degree of consistency (YES in step S207), the determination function 125 determines a procedure having a highest priority among the plurality of candidate procedures having the highest degree of consistency as a recommended procedure (step S208).

On the other hand, when it is determined that the candidate procedures do not include a plurality of procedures having the highest degree of consistency in step S207 (NO in step S207), that is, when the plurality of candidate procedures include only a single procedure having the highest degree of consistency, the determination function 125 determines the procedure having the highest degree of consistency as a recommenced procedure (step S209).

Although an example in which a single recommended procedure is determined on the basis of priorities and degrees of consistency in set images when a plurality of candidate procedures are extracted in the automatic mode has been described here, the determination function 125 may be configured to cause a user to select a single procedure from candidate procedures even in the automatic mode as in the manual mode.

In addition, the recommended procedure determination processing may be processing capable of determining a single recommended procedure from a plurality of candidate procedures and need not necessarily have all steps of determination processing illustrated in FIG. 8. For example, the recommended procedure determination processing may be processing for determining a recommended procedure on the basis of only degrees of consistency, processing for determining a recommended procedure according to whether candidate procedures have the same set image, processing for determining a recommended procedure on the basis of only priority, or processing for determining a recommended procedure by combining one or more of these conditions. In addition, when it is impossible to narrow down recommended procedures to one on any condition, the recommended procedure determination processing may be configured to cause a user to appropriately select a recommended procedure.

The ultrasonic diagnostic device 100 of the embodiment configured in this manner determines a recommended procedure on the basis of degrees of consistency between an ultrasonic image acquired in the current procedure and set images registered in association with each procedure during execution of a target protocol including one or more procedures. Alternatively, the ultrasonic diagnostic device 100 of the embodiment determines a recommended step on the basis of set images registered in the current procedure and set images registered in procedures other than the current procedure. By including such a configuration, the ultrasonic diagnostic device 100 of the embodiment can improve convenience of the examination supporting function (so-called protocol assistant) of proceeding with an examination according to a protocol registered in advance.

For example, the ultrasonic diagnostic device 100 of the embodiment may determine a procedure having a set image with a high degree of consistency with an ultrasonic image acquired in the current procedure that is being executed as a recommended procedure. Therefore, according to the ultrasonic diagnostic device 100 of the embodiment, a procedure capable of acquiring an ultrasonic image through the same operation as the current procedure is determined as a recommended procedure and thus a user can proceed with an examination with high efficiency.

In addition, the ultrasonic diagnostic device 100 of the embodiment executes a recommended procedure when the recommended procedure is determined and execution initiation conditions for the recommended procedure with respect to the current procedure are satisfied. Therefore, according to the ultrasonic diagnostic device 100 of the embodiment, it is possible to start the recommended procedure at an appropriate timing during operation in the automatic mode.

Furthermore, the ultrasonic diagnostic device 100 of the embodiment causes a user to select a recommended procedure form a plurality of candidate procedures that can be recommended procedures when the plurality of candidate procedures have been extracted. Therefore, according to the ultrasonic diagnostic device 100 of the embodiment, the user can also perform an examination having somewhat high degree of freedom even when the automatic mode is selected.

In addition, the ultrasonic diagnostic device 100 of the embodiment notifies a user of one or more candidate procedures that can be a recommended procedure with respect to the current procedure when the candidate procedures have been extracted and executes a recommended procedure in response to input of an operation of selecting any candidate procedure as the recommended procedure. Therefore, according to the ultrasonic diagnostic device 100 of the embodiment, the user can perform an examination with a high degree of freedom at a timing convenient for the user by selecting the manual mode.

Furthermore, in the ultrasonic diagnostic device 100 of the embodiment, a set image can be set as a reference image that can be displayed along with an ultrasonic image acquired in the current procedure or an image associated with the reference image. Therefore, according to the ultrasonic diagnostic device 100 of the embodiment, when an ultrasonic image has been registered as a reference image of a procedure, a recommended procedure can be determined by setting the reference image as a set image. Further, when an image (e.g., an illustration image or the like) inappropriate to be compared to an ultrasonic image has been registered as a reference image of a procedure, a recommended procedure can be determined by setting an ultrasonic image acquired in past execution of the procedure, or the like as a set image.

In addition, the ultrasonic diagnostic device 100 of the embodiment provides a user interface for instructing other steps to be executed instead of a recommended procedure during execution of the recommended procedure. Therefore, according to the ultrasonic diagnostic device 100 of the embodiment, a user can rapidly change a procedure that is being executed to another procedure even when an executed recommended procedure is not a procedure expected by the user.

Furthermore, the ultrasonic diagnostic device 100 of the embodiment sets procedures that are procedures included in a protocol that is being performed, procedures included in a protocol that is not being performed or procedures that are not included in any protocol and are different from the current procedure as candidate procedure extraction targets. Therefore, according to the ultrasonic diagnostic device 100 of the embodiment, a user can select and execute a more appropriate procedure according to the necessity at the time of examination even when procedures are not included in the protocol that is being performed.

In addition, the ultrasonic diagnostic device 100 of the embodiment excludes completed procedures from candidate procedure extraction targets and adds procedures canceled from completion to the extraction targets. Therefore, according to the ultrasonic diagnostic device 100 of the embodiment, a completed procedure can be curbed from being erroneously executed and a user can easily resume a procedure according to the necessity at the time of examination even if the procedure has been completed once.

Modified Examples

The control function 123 may be configured to have a function of storing ultrasonic images acquired by the image acquisition function 121 and to calculate a degree of consistency using the stored ultrasonic images. By including such a configuration, the ultrasonic diagnostic device 100 of an embodiment can calculate a degree of consistency independently of display of an ultrasonic image. Therefore, according to the ultrasonic diagnostic device 100 configured in this manner, it is possible to suggest a recommended procedure based on an ultrasonic image that is being displayed even in a case where reproduction of an ultrasonic image is temporarily stopped, a case where a recorded ultrasonic image is reproduced, and the like, for example.

The extraction function 124 may be configured to extract candidate procedures on the basis of set images set in the current procedure and set images set in procedures other than the current procedure instead of an ultrasonic image acquired in the current procedure. For example, the extraction function 124 may extract procedures having the same set image as that of the current procedure as candidate procedures. According to the ultrasonic diagnostic device 100 configured in this manner, the processing time taken to extract candidate procedures can be reduced because calculation of degrees of consistency is not necessarily required. Further, the ultrasonic diagnostic device 100 may be configured to be able to change a method of extracting candidate procedures on the basis of degrees of consistency (hereinafter referred to as a "first extraction method") and a method of extracting candidate procedures on the basis of set images of the current procedure (hereinafter referred to as a "second extraction method") according to settings and the like.

In addition, when a plurality of procedures in which the same set image as that of the current procedures is set are present in the second extraction method, the determination function 125 may be configured to cause a user to select a recommended procedure from the procedures using the procedures as candidate procedures. In this case, the determination function 125 may determine a recommended procedure on the basis of priority of set images. In this case, the determination function 125 may determine, as a recommended procedure, a procedure having the same scan mode as that of the current procedure among candidate procedures having the same set image as that of the current procedure. In addition, the procedure having the same scan mode as that of the current procedure may be extracted as a candidate procedure. In this case, the control function 123 may be configured to automatically execute a procedure having a highest priority among candidate procedures as a recommended procedure when execution initiation conditions are satisfied.

The control function 123 may be configured to notify that it is necessary to change an ultrasonic probe in execution of a recommended procedure when an ultrasonic probe used in the recommended procedure is different from an ultrasonic probe used in the current procedure. In addition, this notification may be performed by the determination function 125 when a user is caused to select a recommended procedure. For example, in this case, the determination function 125 may list candidate procedures along with information representing whether it is necessary to change an ultrasonic probe 10 when each candidate procedure is executed. Further, when it is necessary to change the ultrasonic probe 10, the control function 123 or the determination function 125 may be configured to notify of whether the ultrasonic probe 10 needs to be changed and information representing an ultrasonic probe 10 that is a change destination (e.g., a connection port number of the ultrasonic probe 10, or the like). According to the ultrasonic diagnostic device 100 configured in this manner, a user can clearly ascertain that a probe used in a procedure that is being executed needs to be changed to another probe when a recommended procedure is used and can smoothly proceed with examination. In addition, the user can select a recommended procedure including whether a probe needs to be changed.

The control function 123 may be configured to cause a user to select a procedure to be executed instead of a recommended procedure that is being executed from candidate procedures from which the recommended procedure has been selected when a state in which there is no input operation of the user with respect to the recommended procedure continues for a certain time or longer during execution of the recommended procedure. According to the ultrasonic diagnostic device 100 configured in this manner, it is possible to suggest other recommended procedures to the user when an operation of the user does not smoothly progress during execution of the recommended procedure.

Although a protocol is generally defined by one or more procedures and an execution order thereof, a recommended procedure that is recommended to be executed subsequent to the current procedure or instead of the current procedure can be executed in the ultrasonic diagnostic device 100 of the present embodiment. Accordingly, procedures are not necessarily executed in a preset execution order in the ultrasonic diagnostic device 100 of the present embodiment. Therefore, a protocol does not necessarily define a procedure execution order and may be defined as a simple set of one or more procedures in the ultrasonic diagnostic device 100 of the present embodiment.

According to at least one embodiment described above, an image acquisition unit which acquires an ultrasonic image of a subject based on an output signal of an ultrasonic probe, a control unit which, for each of one or more examination procedures registered in advance including one or more steps including processing of acquiring the ultrasonic image, in which set images are associated and registered, executes processing for each of the steps, and a determination unit which determines a recommended step recommended to be executed subsequent to a current step or instead of the current step on the basis of a degree of consistency between a set image registered for each of the steps and an ultrasonic image acquired in the current step that is being executed or determines a recommended step recommend to be executed subsequent to the current step or instead of the current step on the basis of set images registered in the current step that is being executed and set images set in steps other than the current step are included, wherein the control unit can execute a recommended step subsequent to the current step or instead of the current step when the recommended step has been determined during execution of the current step to improve convenience of the examination supporting function of proceeding with examination according to a procedure registered in advance.

Although several embodiments have been described, these embodiments have been suggested as examples and are not intended to limit the scope of the invention. These embodiments can be implemented in other various forms and various omissions, substitutions and modifications are possible without departing from essential characteristics of the invention. These embodiments and modifications thereof are included in the scope and essential characteristics of the invention and also included in the invention disclosed in claims and the equivalents thereof.

What is claimed is:

1. An ultrasonic diagnostic device, comprising:
processing circuitry configured to
acquire an ultrasonic image of a subject based on an output signal of an ultrasonic probe,
execute processing for each step for each of one or more examination procedures registered in advance and including one or more steps including processing of acquiring the ultrasonic image,
execute a recommended step subsequent to a current step or instead of the current step when an operation is performed to select the recommended step from among one or more candidate steps that are candidates for the recommended step, and
cause a display to display the ultrasonic image,
wherein the recommended step is a step that is recommended to be executed subsequent to the current step being executed or instead of the current step based on set images set for each of the one or more steps for each of the one or more examination procedures, and
wherein the processing circuitry is further configured to compare a set image set for the current step with the set images set for each step other than the current step, and select one or more steps having the same set image as that of the current step as the one or more candidate steps, based on a result of comparison between the set images.

2. A non-transitory computer-readable recording medium storing a program that, when executed, causes a computer to:
acquire an ultrasonic image of a subject based on an output signal of an ultrasonic probe;
execute processing for each step for each of one or more examination procedures registered in advance and including one or more steps including processing of acquiring the ultrasonic image,
execute a recommended step subsequent to a current step or instead of the current step when an operation is performed to select the recommended step from among one or more candidate steps that are candidates for the recommended step, and
cause a display to display the ultrasonic image,
wherein the recommended step is a step that is recommended to be executed subsequent to the current step being executed or instead of the current step based on set images set for each of the one or more steps for each of the one or more examination procedures, and
wherein the program further causes the computer to compare a set image set for the current step with the set images set for each step other than the current step, and select one or more steps having the same set image as that of the current step as the one or more candidate steps, based on a result of comparison between the set images.

3. The ultrasonic diagnostic device according to claim 1, wherein the processing circuitry is further configured to determine the recommended step and execute the recommended step when execution initiation conditions for the recommended step with respect to the current step are satisfied.

4. The ultrasonic diagnostic device according to claim 1, wherein, when an ultrasonic probe used in the recommended step is different from an ultrasonic probe used in the current step, the processing circuitry is further configured to notify that it is necessary to change the ultrasonic probe in execution of the recommended step.

5. The ultrasonic diagnostic device according to claim 1, wherein the set images are reference images that are displayed along with the ultrasonic image acquired in the current step or images associated with the reference images.

6. The ultrasonic diagnostic device according to claim 1, wherein the processing circuitry is further configured to provide a user interface for instructing another step instead of the recommended step to be executed during execution of the recommended step.

* * * * *